US008226648B2

(12) United States Patent  
Paul et al.

(10) Patent No.: US 8,226,648 B2
(45) Date of Patent: *Jul. 24, 2012

(54) PRESSURE-SENSITIVE FLEXIBLE POLYMER BIPOLAR ELECTRODE

(75) Inventors: Saurav Paul, Minnetonka, MN (US); Harry Puryear, Shoreview, MN (US); Chou Thao, Brooklyn Park, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1242 days.

This patent is subject to a terminal disclaimer.

(21) Appl. No.: 11/968,044

(22) Filed: Dec. 31, 2007

(65) Prior Publication Data
US 2009/0171343 A1  Jul. 2, 2009

(51) Int. Cl.
*A61B 18/14*  (2006.01)

(52) U.S. Cl. .......................................... 606/50; 606/41

(58) Field of Classification Search .................. 606/41, 606/48, 50
See application file for complete search history.

(56) References Cited

U.S. PATENT DOCUMENTS

| | | | |
|---|---|---|---|
| 4,074,718 A * | 2/1978 | Morrison, Jr. .................. 606/45 |
| 5,396,887 A | 3/1995 | Imran | |
| 5,409,008 A | 4/1995 | Svenson et al. | |
| 5,997,532 A | 12/1999 | McLaughlin et al. | |
| 6,032,077 A | 2/2000 | Pomeranz | |
| 6,063,022 A | 5/2000 | Ben-Haim | |
| 6,646,540 B1 * | 11/2003 | Lussey ............................. 338/47 |
| 6,689,128 B2 | 2/2004 | Sliwa, Jr. et al. | |
| 6,701,931 B2 | 3/2004 | Sliwa, Jr. et al. | |
| 7,883,508 B2 * | 2/2011 | Thao et al. ....................... 606/40 |
| 7,955,326 B2 * | 6/2011 | Paul et al. ........................ 606/40 |
| 2002/0115958 A1 | 8/2002 | Nyhart, Jr. | |
| 2002/0123749 A1 * | 9/2002 | Jain .................................. 606/41 |
| 2004/0150322 A1 | 8/2004 | Busta | |
| 2004/0220511 A1 | 11/2004 | Scott et al. | |
| 2005/0090881 A1 * | 4/2005 | Frank et al. .................... 607/105 |
| 2005/0192568 A1 * | 9/2005 | Truckai et al. .................. 606/51 |
| 2006/0137464 A1 * | 6/2006 | Baudendistel .................. 73/779 |
| 2007/0197896 A1 | 8/2007 | Moll et al. | |
| 2007/0244520 A1 | 10/2007 | Ferren et al. | |
| 2007/0250050 A1 | 10/2007 | Lafontaine | |
| 2007/0265610 A1 | 11/2007 | Thapliyal et al. | |
| 2007/0287999 A1 | 12/2007 | Malecki et al. | |
| 2007/0299492 A1 | 12/2007 | Zhang et al. | |
| 2008/0161794 A1 * | 7/2008 | Wang et al. ...................... 606/41 |

OTHER PUBLICATIONS

International Search Report and Written Opinion for PCT/US2008/087119 mailed Feb. 18, 2009.

* cited by examiner

*Primary Examiner* — Michael Peffley
*Assistant Examiner* — Samantha Good
(74) *Attorney, Agent, or Firm* — Dykema Gossett PLLC

(57) ABSTRACT

The present invention is directed to bipolar ablation systems. A bipolar electrode system for ablation therapy is disclosed, including a pressure-sensitive conducting composite layer and a pair of electrodes in electrical conductive contact or communication with the pressure-sensitive conducting composite layer. Energy (e.g., ablation energy) is delivered via the pressure-sensitive conductive composition when sufficient pressure is applied to transform the pressure-sensitive conductive composite to an electrical conductor. An electrically insulative flexible layer, which may include a passageway for a fill material is also disclosed. In some embodiments, the systems can also be used for targeted delivery of compounds, such as drugs, using a bipolar electrode.

30 Claims, 5 Drawing Sheets

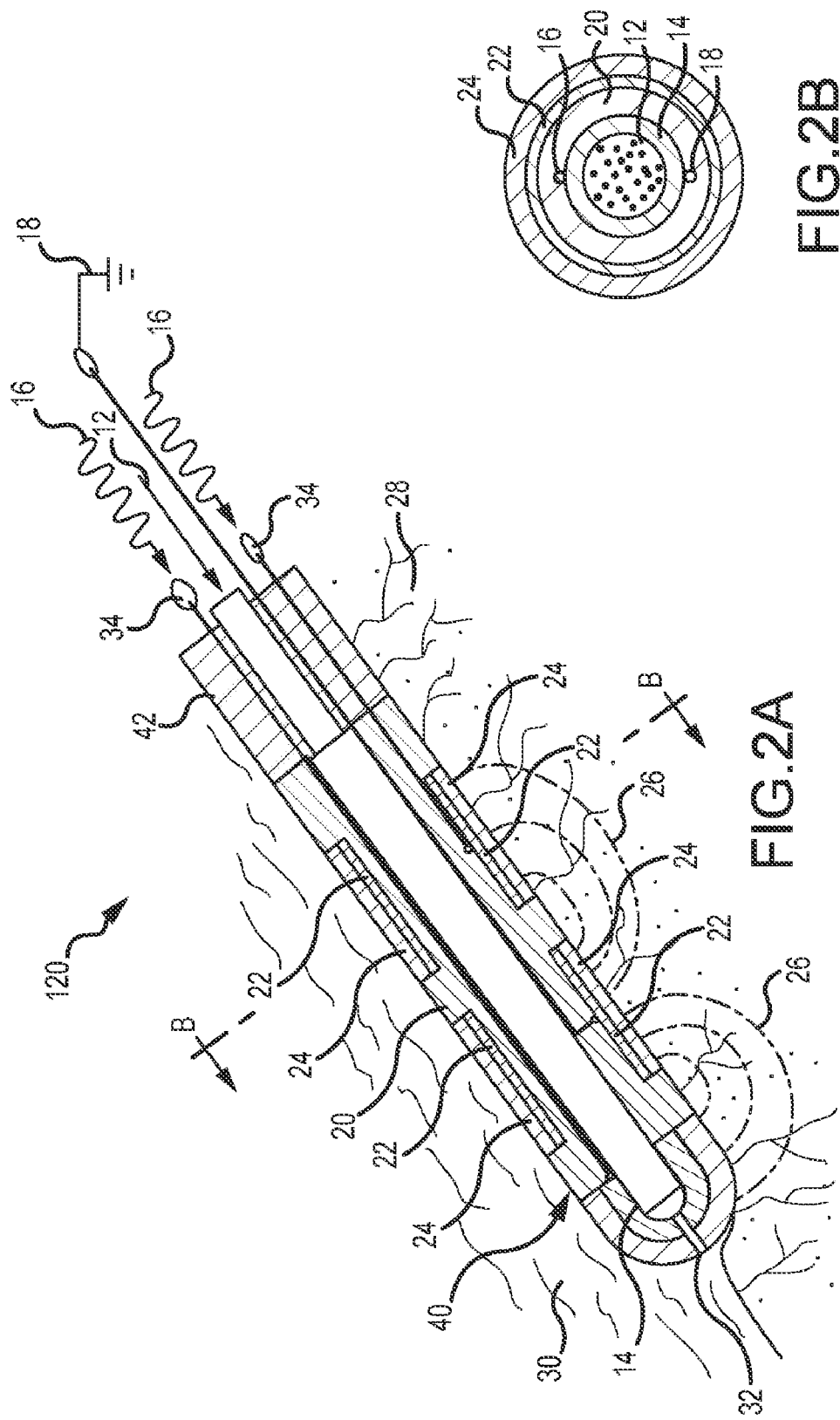

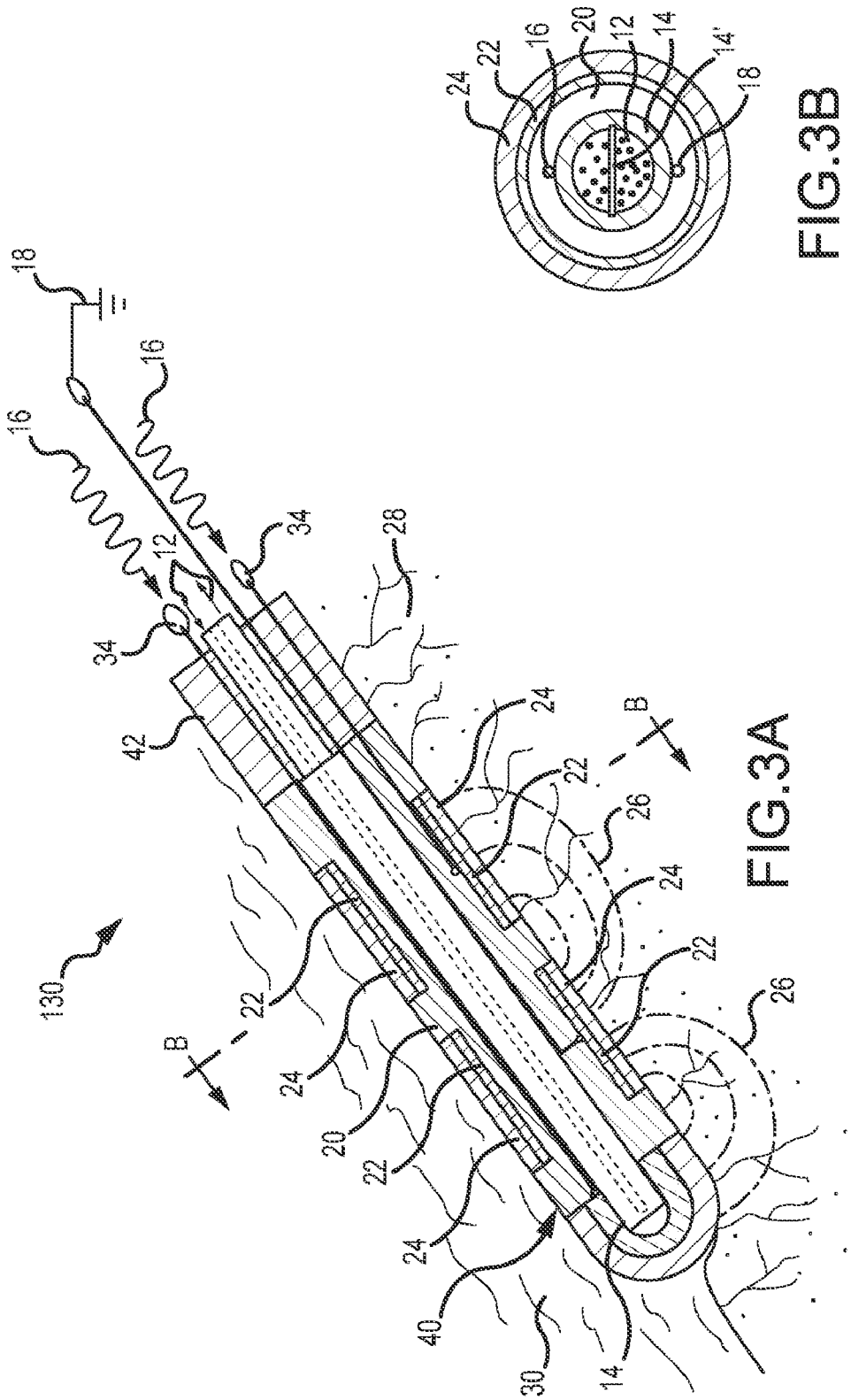

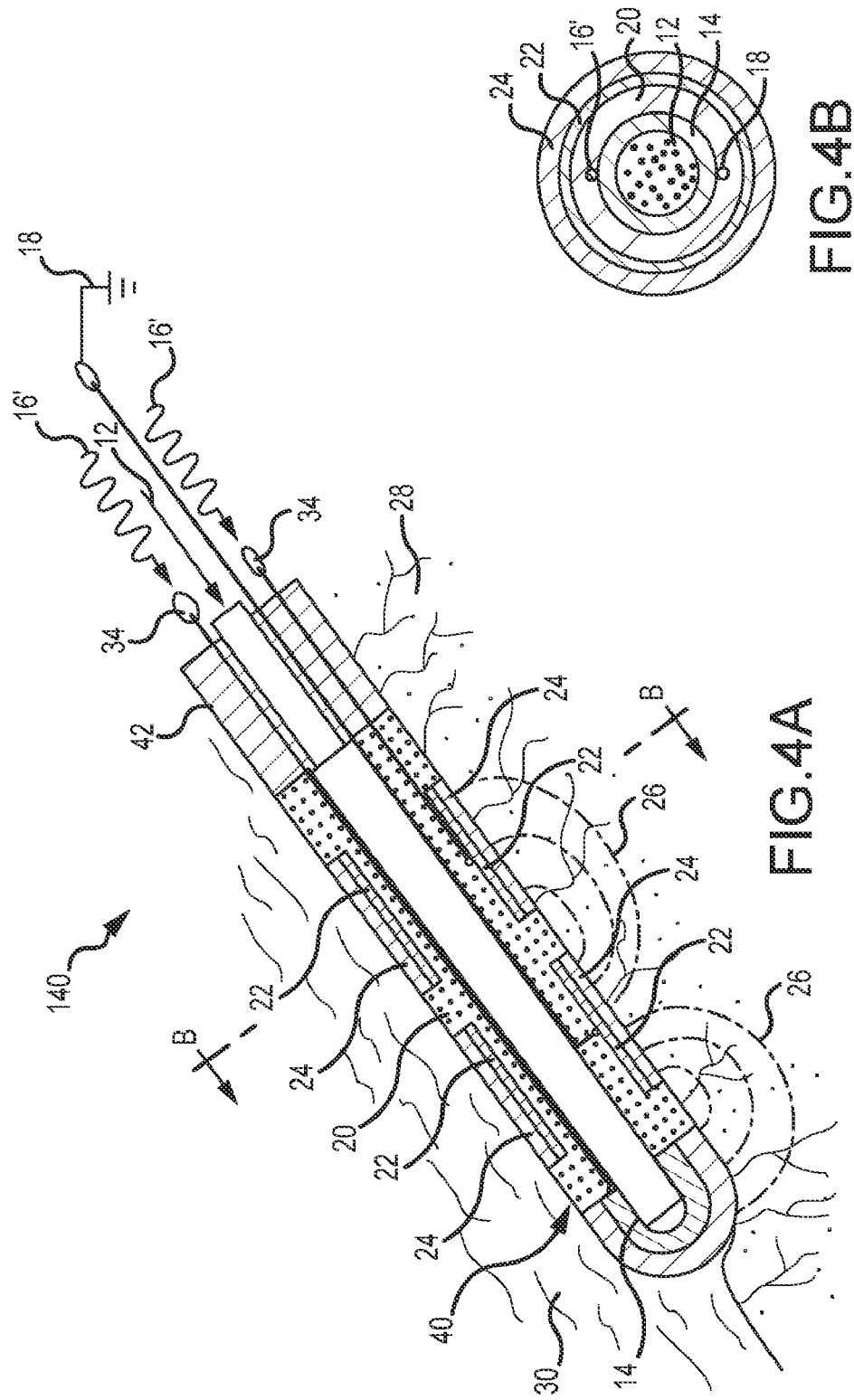

PRESSURE-SENSITIVE FLEXIBLE POLYMER BIPOLAR ELECTRODE

CROSS-REFERENCE TO RELATED APPLICATIONS

Not applicable.

BACKGROUND OF THE INVENTION a. Field of the Invention

The present invention pertains generally to an electrophysiological device and method for providing energy to biological tissue and, more particularly, to an ablation apparatus that includes a bipolar electrode that uses a flexible polymer electrode. The present invention is also directed to an electrophysiological device that can be used for drug delivery to a target tissue.

b. Background Art

In a normal heart, contraction and relaxation of the heart muscle (myocardium) takes place in an organized fashion as electrochemical signals pass sequentially through the myocardium from the sinoatrial (SA) node located in the right atrium to the atrial ventricular (AV) node and then along a well defined route which includes the His-Purkinje system into the left and right ventricles. Sometimes abnormal rhythms occur in the atrium, a condition known as atrial arrhythmia. Three of the most common arrhythmia are: (1) ectopic atrial tachycardia, (2) atrial fibrillation, and (3) atrial flutter. Arrhythmia can result in significant patient discomfort and even death because of a number of associated problems, including: (1) an irregular heart rate, which causes a patient discomfort and anxiety; (2) loss of synchronous atrioventricular contractions which compromises cardiac hemodynamics resulting in varying levels of congestive heart failure; and (3) blood flow stasis, which increases the vulnerability to thromboembolism. It is sometimes difficult to isolate a specific pathological cause for the arrhythmia, although it is believed that the principal mechanism is one or a multitude of stray circuits within the left and/or right atrium. These circuits or stray electrical signals are believed to interfere with the normal electrochemical signals passing from the SA node to the AV node and into the ventricles. Efforts to alleviate these problems in the past have included administering various drugs. In some circumstances, drug therapy is ineffective and frequently is plagued with side effects, such as dizziness, nausea, vision problems, and other difficulties.

For example, an increasingly common medical procedure for the treatment of certain types of cardiac arrhythmia and atrial arrhythmia involves ablation of heart tissue to cut off the path for stray or improper electrical signals. Such procedures may be performed by catheters that incorporate ablation electrodes. Typically, the catheter is inserted in an artery or vein in the leg, neck, or arm of the patient and threaded, sometimes with the aid of a guidewire or introducer, through the vessels until a distal tip of the catheter reaches the desired location for the ablation procedure in the heart. During the ablation procedure, the electrode of the ablation catheter is placed in contact with the target tissue and therapeutic substance is applied to the tissue via the electrode. Therapeutic substance may be a chemical substance; energy, such as thermal energy (heating or cooling); electrical energy, such as radiofrequency (RF) current; electromagnetic energy, such as light; and acoustic energy, such as ultrasound. Upon delivery of sufficient therapeutic substance to the tissue, the ablation procedure kills and/or irreversibly modifies the target tissue, and produces lesions. The lesion partially or completely blocks the stray electrical signals to lessen or eliminate arrhythmia.

Efficacious delivery of therapeutic substance from the electrode to the target tissue requires that the electrode to be in optimal contact with the target tissue. Ensuring optimal contact between the electrode and the tissue is not readily achieved using rigid electrodes, such as metal electrodes. Several factors that may contribute to suboptimal contact include: (i) the remote manipulation of the catheter from the electrode, typically over four feet away; (ii) the constant movement of the heart wall; (iii) the variable compliance of the heart wall, and (iv) the highly contoured nature of the heart wall. Flexible polymer electrodes are designed to provide superior conformance with tissue than metal electrodes.

BRIEF SUMMARY OF THE INVENTION

In a first aspect, the invention is directed to a bipolar electrode system for ablation therapy, comprising a pressure-sensitive conducting composite layer and at least a pair of electrodes in electrical conductive contact or communication with the pressure-sensitive conducting composite layer. The bipolar electrode system may include a catheter base that is coupled to the conductive element and/or the pressure-sensitive conductive composite. An energy source may be coupled to the pair of electrodes, such that energy (e.g., ablation energy) is delivered via the pressure-sensitive conductive composition when sufficient pressure is applied to transform the pressure-sensitive conductive composite to an electrical conductor. An electrically insulative flexible layer, which may include a passageway for a fill material, may be found adjacent to the pressure-sensitive conductive layer. Sensors may also be located in the electrically insulative flexible layer for monitoring temperature, such as at an outlet coupled to a passageway for a fill material, or elsewhere. In those cases where an outlet is present, the outlet may permit flowable filler material to flow from the passageway. Additionally, a heat sink may be thermally coupled to the pressure-sensitive conductive composite member and/or to the electrically insulative flexible layer. In those electrodes where a passageway is found in the insulative flexible layer, there may also be found a wall such that flowable fill material circulates in the insulative flexible layer. The electrically insulative flexible layer itself may be permeable or non-permeable. In those bipolar electrode systems that include a passageway for a filler material and where the filler material cools the electrode during ablation, the passageway can be a loop such that a cooling fluid travels from a proximal end of the electrode through a distal end of the electrode and returns to the proximal end of the electrode via the passageway.

In another aspect, the present invention is direct to a bipolar electrode for ablation therapy that comprises a pressure-sensitive conducting composite layer, an electrically insulative flexible tube adjacent the pressure-sensitive conducting composite layer, at least a pair of electrodes in electrical conductive contact or communication with the pressure-sensitive conducting composite layer, and a passageway for a filler material in the electrically insulative flexible tube.

In yet another aspect, the invention is directed to methods of treating a target tissue. A bipolar electrode system having a pair of electrodes for conducting RF energy and a layer of pressure-sensitive conductive composite that is in electrical contact or communication with at least a portion of the pair of electrodes are coupled to an RF energy supply; the bipolar electrode system is operatively contacted with a target tissue of a subject; pressure is exerted upon the target tissue through the electrode such that the pressure-sensitive conductive composite becomes conductive, delivering energy to the target tissue. The method can include communicating with a heat sink thermally coupled to the bipolar electrode system.

In another aspect, the invention is directed to a bipolar electrode for ablation therapy that includes a catheter having a proximal end and a distal end, at least a pair of electrodes for conducting energy, and a layer of quantum tunneling composite that is in electrical communication with the pair of electrodes, where the layer is located at least in part at a distal end of the catheter. The bipolar electrode can also include an electrically insulative flexible tube thermally adjacent to the pressure-sensitive conducting composite layer. The electrode can also include at least one sensor to measure the temperature of the electrically insulative flexible tube, and/or a heat sink that is coupled to at least the quantum tunneling composite layer or the electrically insulative flexible tube.

In yet another aspect, the invention is directed to a bipolar electrode assembly for conducting ablative energy, where the assembly comprises a pair of electrodes for conducting the ablative energy, a quantum tunneling composite member, and an energy source coupled to the quantum tunneling composite member, wherein the pair of electrodes is disposed relative to the quantum tunneling composite member such that pressure that is applied to the pair of electrodes is transferred to the quantum tunneling composite member and causes the quantum tunneling composite member to become electrically conductive such that it conducts electrical energy to the electrode. The electrode assembly can also include a conductor that is in electrical contact or communication with the quantum tunneling composite member, where the conductor is configured to conduct electrical energy sufficient to cause ablation. The electrode may be located on a distal end of the electrode assembly, and the quantum tunneling composite member may be disposed in physical contact or communication with the electrode along the longitudinal axis of the electrode assembly. The electrode assembly can also include at least one pressure transfer member disposed between the quantum tunneling composite member and the electrode, such that pressure applied to the electrode is transferred through at least one pressure transfer member to the quantum tunneling composite member. A processor that can sense the degree of contact between the electrode and the surface of a tissue to be ablated can also be included in the assembly. A processor that monitors for a change in impedance of the quantum tunneling composite member can also be included with the electrode assembly, where the processor is coupled to a generator to control the energy being generated based on a change in impedance of the quantum tunneling composite member.

In another aspect, the invention is directed to a method of delivering a compound to a target tissue, where a bipolar electrode system that has a pair of electrodes for conducting DC and RF energy and a layer of pressure-sensitive conductive composite that is in electrical contact or communication with at least a portion of the pair of electrodes is coupled to a DC energy supply to the pair of electrodes and with a circulating a flowable filler material that includes the compound to be delivered to the target tissue. The system is operatively contacted to the bipolar electrode system with a target tissue of a subject; the DC energy supply is engaged, and then an effective amount of pressure is exerted upon the target tissue through the electrode such that the pressure-sensitive conductive composite becomes conductive and delivers DC energy to the target tissue. The method can also include coupling an RF energy supply to the pair of electrodes. The method can also include the steps of, after delivering DC energy to the target tissue, disengaging the DC energy supply, engaging a RF energy supply coupled to the pair of electrodes, and exerting an effective amount of pressure upon the target tissue through the electrode such that the pressure-sensitive conductive composite becomes conductive and delivers RF energy to the target tissue. Compounds that can be delivered include those that are electrophoretic and photosensitive, for example.

BRIEF DESCRIPTION OF THE DRAWINGS

FIGS. 2A-2B depict an embodiment of a PSCC electrode that includes an outlet.

FIGS. 3A-3B show another embodiment of a PSCC electrode that does not include an outlet.

FIGS. 4A-4B show the direction of ablative energy from the embodiment of a PSCC electrode shown in FIGS. 3A-3B.

DETAILED DESCRIPTION OF THE INVENTION

Figure 1A:
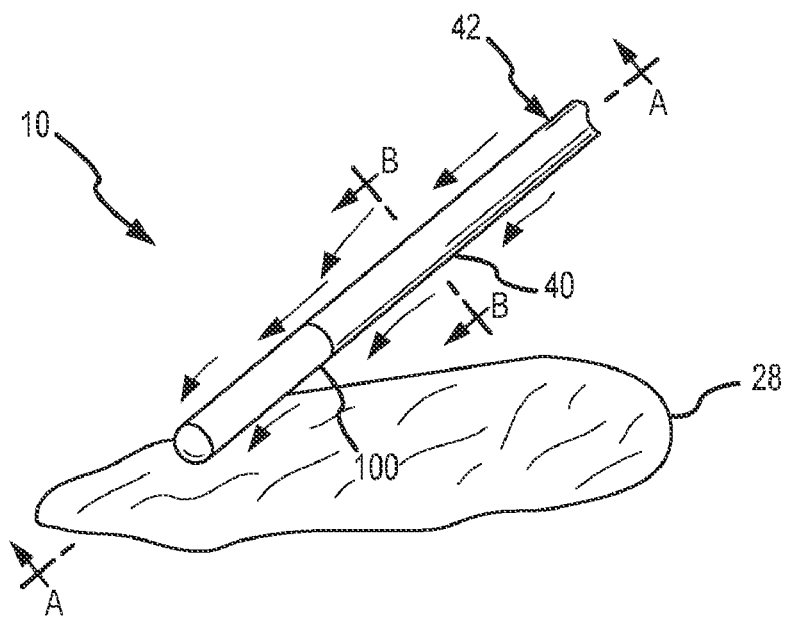
FIGS. 1A-1B show a general scheme of a pressure-sensitive conductive composite (PSCC) electrode as applied to a target tissue.

Pressure-sensitive conductive composite (PSCC) electrodes are disclosed, along with methods for using an electrode for tissue ablation and targeted drug delivery.

As used herein, "pressure-sensitive polymer," "pressure-sensitive composite" and "PSCC" generally mean a pressure-sensitive conductive composite that has unique electrical properties wherein the electrical resistance of the PSCC varies inversely in proportion to the pressure that is applied to the PSCC. Useful PSCCs commonly have a high electrical resistance when quiescent (not under pressure), and become conductive under pressure, where the electrical resistance may fall, for example, to less than one ohm. When quiescent, the PSCC material can have a resistance that is greater than 100,000 ohms to greater than 1M ohms, and as a non-conductor (e.g., having a resistance greater than 10M ohms).

The present invention can use various pressure-sensitive conductive composite materials. For example, U.S. Pat. No. 6,999,821 discloses conductor-filled polymers that can include presently available materials approved for implantation in a human body such as silicone rubber with embedded metallic, carbon or graphite particles or powder. For example, silver-filled silicone rubbers, such as NuSil R2637 (NuSil; Carpinteria, Calif.) and similar products from Specialty Silicone Products (Ballston Spa, N.Y.) can be used. Other insulating or weakly conductive materials (e.g., non-conductive elastomers) can be embedded with conductive materials, conductive alloys and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium and metals of the lanthanide and actinide series and, if appropriate, at least one electroconductive agent). The conductive material can comprise a powder, grains, fibers or other shaped forms. The oxides can be mixtures comprising sintered powders of an oxycompound. The alloy can be conventional, such as, for example, titanium boride.

Other examples of PSCCs that can be suitable for use in connection with embodiments of the present invention include quantum tunneling composites ("QTC"), such as those available through Peratech Ltd. (Darlington, UK), and include the QTC pill, the QTC substrate and the QTC cables. QTC materials can have variable resistance values that range from >10 M ohms (in the absence of stress) to <1 ohm when under pressure.

Other examples of PSCC materials that can be used in the present invention include the conductive polymers disclosed in U.S. Pat. Nos. 6,646,540, 6,495,069, and 6,291,568. These materials can have a variable resistance of $>10^{12}$ ohms before any stress is applied to less than 1 ohm when finger pressure is applied.

As a result of this unique property, PSCC materials have the ability to transform from an effective insulator to a metal-like conductor when deformed by compression, twisting, or stretching. The electrical response of a PSCC can be tuned appropriately to the spectrum of pressures being applied. Its resistance range often varies from greater than 10 M ohms to less than 1 ohms. The transition from insulator to conductor often follows a smooth and repeatable curve, with the resistance dropping monotonically to the pressure applied. Moreover, the effect is reversible once the pressure is removed, restoring electrical resistance. Thus, a PSCC may be transformed from an insulator to a conductor, and back to an insulator, simply by applying the appropriate pressure. PSCCs can conduct large currents (up to 10 Amps) and support large voltages (40 V and higher).

The PSCC can transform from an insulator (that is, conducting little or no current) to an effective conductor simply by applying a small change in pressure to the PSCC. For example, by applying pressure with a hand, or more particularly, with a finger, a surgeon can transform the PSCC from an insulator to a conductor to permit contact sensing.

The PSCC can also be chosen or customized to have a specific pressure sensitivity such that the insulator-conductance transition occurs over a wide or narrow range. For example, highly sensitive PSCCs, which register a sharp change in resistance with a finite amount of applied pressure, may be preferred for soft contact applications such as the atrial wall. Less-sensitive PSCCs, which require more pressure to register the same amount of change in resistance, may be preferred for hard contact applications such as ablation in ventricular walls.

Because a PSCC's resistance drops monotonically as pressure increases, a PSCC electrode is able to deliver energy for ablation gradually, and then increasingly as pressure increases.

In an embodiment of the present invention, the electrode is fabricated with a PSCC that differentiates between a soft and a hard push. Such a device can be used to switch, for example, an ablation electrode in response to a concentrated pressure while ignoring the general background pressure. Alternatively, such a device can "turn on" and deliver electrical energy that is already present within the device.

Because PSCC electrode devices and systems may be used to deliver ablation with a "soft start," the PSCC electrode devices and systems of the present invention may be used in direct contact with the target tissue, thereby eliminating the physical gap that sometimes exists with other ablation electrodes. Eliminating the gap can reduce the possibility of arcing, and thereby can improve the safety and efficacy of ablation.

In some embodiments, the PSCC electrode device can contain a filler material that can be used, for example, to cool the device and surrounding tissues, or to carry desired compounds. "Filler material" (e.g., as shown as element 12 in FIGS. 2-5) comprise flowable fillers, such as water, saline, silicone oil; solid fillers, gel fillers, or structured solid-fillers, such as a bundle of acoustics-carrying glass or metal fibers. In the case of flowable and gel fillers, the material need not be physiologically compatible if the filler is isolated from, or briefly contacts, the target and surrounding tissues when using the PSCC electrode device.

Figure 1B:
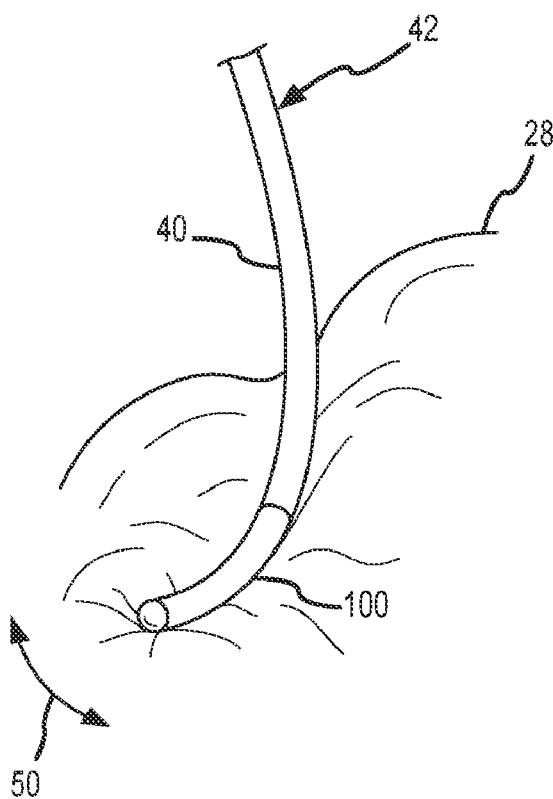

FIGS. 1A and 1B illustrate an overall scheme of the present teaching. PSCC electrode system 10 includes a catheter shaft 42 and a contact surface 100 that extends from catheter shaft 42. The PSCC electrode 40 is flexible such that when it comes into contact with a target tissue 28, PSCC electrode 40 is deflected in direction 50 (e.g., as illustrated in FIG. 1B), and the deflection permits activation of PSCC electrode 40 based on a degree of contact between PSCC electrode 40 and the target tissue 28.

FIG. 2 shows a PSCC electrode system 120 as a first bipolar electrode according to the present teaching. FIGS. 2A and 2B show two cross-sectional drawings taken along the reference lines of A-A (longitudinal) and B-B (cross-sectional) of FIG. 1. As depicted in FIGS. 2A and 2B, the PSCC bipolar electrode system 120 comprises a PSCC electrode 40 that extends from a catheter shaft 42. The PSCC electrode 40 comprises an electrically insulative flexible tube 14 located centrally in the electrode 40 and extending into the catheter shaft 42. The electrically insulative flexible tube 14 may include a filler material 12. An efflux outlet 32 may be connected to the electrically insulative flexible tube 14 and, in the case of flowable filler material 12, can allow such filler material 12 to flow from the system 120 to the surrounding area (including the surrounding tissue 30 and the target tissue 28). Returning to the PSCC electrode 40, a PSCC substrate layer 22 may be mechanically connected to the electrically insulative flexible tube 14 and be electrically and mechanically coupled to electrodes 24, such as gold-loaded conductive polymer electrodes. The PSCC substrate 22 may be functionally and electrically connected to one end of electrical conducting element 34. The electrical conducting element 34 is substantially contained within the catheter shaft and is connected at the other end to a current source 16 (e.g., RF current source) or an electrical ground 18. A heat sink 20 may thermally encapsulate, at least partially, the electrically insulative flexible tube 14. The PSCC substrate layer 22 is capable of bending and conforming to a compliant tissue wall of a target tissue 28.

The PSCC bipolar electrode system 120 ablates tissue by delivering ablation energy, depicted in FIG. 2A as electric field 26, via the electrodes 24 when the pressure applied to the PSCC substrate layer 22 as a result of electrode-tissue contact is sufficient to engender or provide an electrical response that is transmitted to the electrodes 24. The applied pressure can be provided and manipulated directly by an operator (such as an operating physician), or indirectly through a mechanical device operably linked to the PSCC electrode 40. The ablation energy 26 is delivered substantially to the target tissue 28 and not to surrounding tissue 30 (e.g., blood) by virtue of activating the PSCC adjacent to the target tissue 28. The pressure sensitivity of the PSCC substrate layer 22 may be adjusted to match the compliance target tissue 28, such that the electrical conductivity of the electrode and the electric field from the electrode is directed substantially to the target tissue 28. The filler material 12 may be in contact with the tissue via outlet 32. In the case of flowable filler material 12, the outlet allows for the flowable filler material 12 to enter the surrounding tissues, e.g., 28, 30.

Having an open system for a flowable filler material 12, shown in FIGS. 2A and 2B, is useful especially for those procedures wherein the flow of the filler material 12 can be easily managed, or may be beneficial to the procedure. An example of such a procedure is endocardial RF ablation. Notably, the filler material 12 can be used to help control the temperature of the electrode system 120 and the target tissue 28 by providing enhanced cooling effects in addition to the cooling effects of the surrounding tissues such as the flowing blood (e.g., a depicted as 30).

FIG. 3 shows a PSCC electrode system 130 as a second bipolar electrode according to the present teaching. FIGS. 3A and 3B show two cross-sectional views taken along the reference lines of A-A (longitudinal) and B-B (cross-sectional) of FIG. 1. The PSCC bipolar electrode system 130 comprises a PSCC electrode 40 that extends from a catheter shaft 42. The PSCC electrode 40 comprises an electrically insulative flexible tube 14 located centrally in the electrode 40 and extending into the catheter shaft 42. The electrically insulative flexible tube 14 may include a filler material 12. A PSCC substrate layer 22 may be mechanically connected to the electrically insulative flexible tube 14, and be electrically and mechanically coupled to electrodes 24, such as gold-loaded conductive polymer electrodes. The PSCC substrate 22 may be functionally and electrically connected to one end of an electrical conducting element 34. The electrical conducting element 34 is substantially contained within the catheter shaft and is connected at the other end to a current source 16 (e.g., RF current source) or an electrical ground 18. A heat sink 20 may thermally encapsulate, at least partially, the electrically insulative flexible tube 14. The PSCC substrate layer 22 is capable of bending and conforming to a compliant tissue wall of a target tissue 28.

Unlike the first bipolar electrode, as depicted in FIG. 2, the electrically insulative flexible tube 14 in the second bipolar electrode, as depicted in FIG. 3, does not contain an efflux outlet 32. Consequently, any filler material 12 present within the electrically flexible tube 14 does not come in contact with either the target tissue 28 or the surrounding tissue 30. The filler material, if flowable, can then circulate through the thermally insulative flexible tube, which can be aided by the introduction of irrigation channels 14'. Thus, the second bipolar electrode in FIG. 3 comprises a closed-cooling system as opposed to an open-cooling system of the first bipolar electrode in FIG. 2.

The PSCC bipolar electrode system 130 ablates tissue by delivering ablation energy, depicted in FIG. 3A as electric field 26, via the electrodes 24 when the pressure applied to the PSCC substrate layer 22 as a result of electrode-tissue contact is sufficient to engender or provide an electrical response that is transmitted to the electrodes 24. The applied pressure can be provided and manipulated directly by an operator (such as an operating physician), or indirectly through a mechanical device operably linked to the PSCC electrode 40. The ablation energy 26 is delivered substantially to the target tissue 28 and not to surrounding tissue 30 (e.g., blood) by virtue of activating the PSCC adjacent to the target tissue 28. The pressure sensitivity of the PSCC substrate layer 22 may be adjusted to match the compliance target tissue 28, such that the electrical conductivity of the electrode and the electric field from the electrode is directed substantially to the target tissue 28. In this embodiment, filler material 12 may circulate within the inner flexible core 14 or may be stationary there within. Alternatively, if the filler material 12 is flowable and circulates within the inner flexible core, the filler material may be circulated once and then dispersed or disposed of, or may be re-circulated within a loop that is within, or even exterior to the PSCC bipolar electrode system 10 itself. In the case of a filler material 12 that is flowable, such filler material 12 does not enter the surrounding tissues, e.g., 28, 30 when the embodiment shown in FIG. 3 is used.

The PSCC electrode 40 having a closed-cooling system for a flowable filler material 12, as shown in FIG. 3, is useful especially for those procedures wherein the flow of the filler material 12 to the target tissue 28 or other surrounding tissue 30 may be detrimental to the ablation procedure or difficult to manage. An example of such difficulty during a procedure may occur during epicardial RF ablation where, e.g., saline (a flowable filler material 12) may flow through the efflux outlet of the electrode 40 into the pericardial sac and conduct ablation energy to non-targeted tissues. A critical aspect of epicardial ablation is the functional nature of the surrounding tissue 30; as opposed to flowing blood in endocardial ablation procedures, the pericardial fluid with the pericardial sac does not provide significant additional (convective) cooling of electrode and the target tissue. Thus, the filler material 12 within a closed-cooling system can be used to help control the temperature of the electrode system 130. Additionally, the closed-loop irrigation system can provide interfacial cooling as well as cooling of the adjoining tissues, thus minimizing risk of collateral damage. Furthermore, a cooled interface allows high energy applications during ablation without causing may be used also allow for creating deeper lesions as is customarily required in treating ventricular tachycardia.

FIG. 4 shows yet another embodiment of the present invention, which can be used for ablation as well as for electroporation for delivery of chemicals, for example, electrophoretic compounds, such as drugs, to a targeted tissue. The main difference from this embodiment when compared to those shown in FIGS. 2 and 3 is that the heat sink 20 and the electrically insulative flexible tube 14 are porous or otherwise permeable, allowing molecules of the chemicals to pass through the walls. The molecules can be loaded with a filler material 12.

FIG. 4 shows a PSCC electrode system 140 as a third bipolar electrode according to the present teaching. FIGS. 4A and 4B show two cross-sectional views taken along the reference lines of A-A (longitudinal) and B-B (cross-sectional) of FIG. 1. The PSCC bipolar electrode system 140 comprises a PSCC electrode 40 that extends from a catheter shaft 42. The PSCC electrode itself 40 comprises a electrically insulative flexible tube 14 located centrally in the electrode 40 and extends into the catheter shaft 42; the electrically insulative flexible tube 14 may include a filler material 12 which may contain compounds to be delivered to a target tissue 28. Optionally, an efflux outlet 32 can be connected to the electrically insulative flexible tube 14 and, in the case of flowable filler material 12, can allow such filler material 12 to flow from the system 140 to the surrounding area (including the surrounding tissue 30 and the target tissue 28). Returning to the PSCC electrode 40, a PSCC substrate layer 22 may be mechanically connected to the electrically insulative flexible tube 14 and may be electrically and mechanically coupled to electrodes 24, such as gold-loaded conductive polymer electrodes and wet porous polymer electrodes. The PSCC substrate 22 may be functionally and electrically connected to one end of electrical conducting element 34. The electrical conducting element 34 is substantially contained within the catheter shaft and is connected at the other end to a current source 16' (e.g. RF and/or direct current source) or an electrical ground 18. The PSCC substrate later 22 may be connected functionally and electrically to electrical conducting element 34 and can also be connected to an electrical ground 18. A heat sink 20 may thermally encapsulate, at least partially, the electrically insulative flexible tube 14. The PSCC substrate layer 22 is capable of bending and conforming to a compliant tissue wall of a target tissue 28.

During electroporation, the bipolar electrodes 26 are energized with direct current 16 to create tissue ablation via cellular necrosis or apoptosis. In other applications, the bipolar electrodes 26 are energized with direct current 16 while the porous distal portion carries electrophoretic agents, such as photosensitive drugs for photodynamic therapy. This electroporation technique therefore provides in situ drug delivery. Such techniques may be used for tissue conditioning as precursor to ablative therapies, such as radiofrequency catheter ablation, ultrasound, and photodynamic therapy. After conditioning the tissue with a drug, the electrodes can be energized in a bipolar setting using RF current.

Figure 5A:
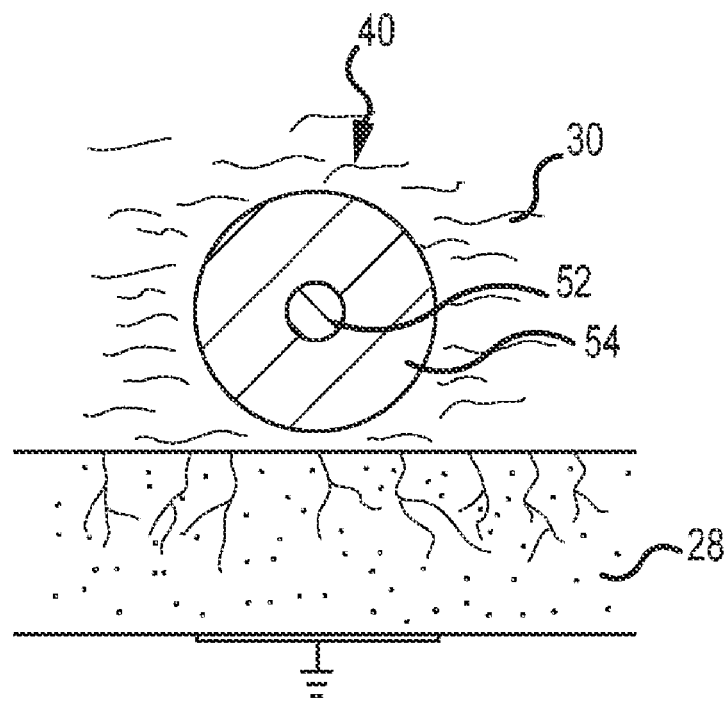
FIGS. 5A-5B illustrate an embodiment of a PSCC electrode than can be used for both ablation and targeted drug delivery.
Figure 5B:
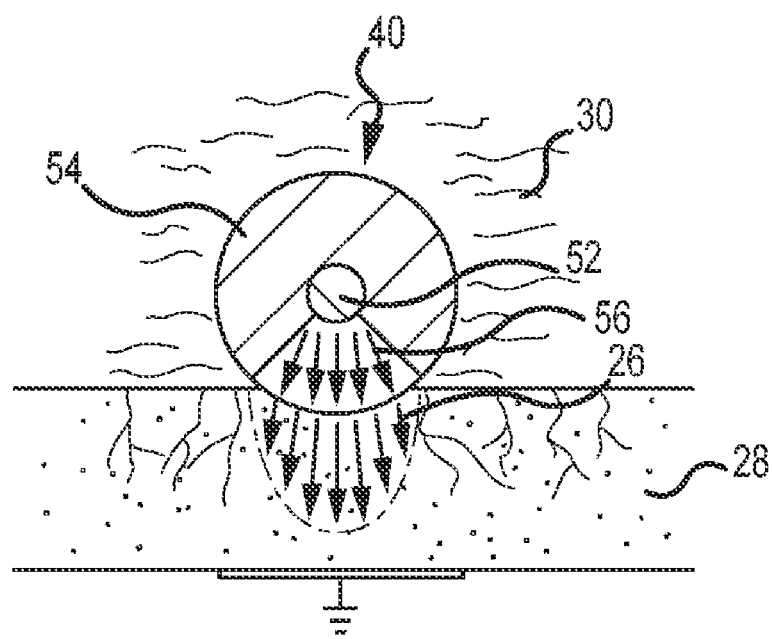

FIG. 5 demonstrates how the PSCC becomes electrically conductive only at the electrode-target tissue wall due to contact pressure. In this case, the ablation energy 26 only flows between the electrodes 24 and into the target tissue 28, but not into surrounding tissue 30. Furthermore, the bipolar configurations, as shown in FIGS. 2, 3 and 4, limit the path of the ablation energy 26 to localized areas in the target tissue 28 near the electrodes 24, thereby preventing the current from escaping into adjacent tissue 30 and causing collateral damage. The electrode shown in FIG. 5 has a conductive core 52, and insulative zone 54. As generally illustrated in the embodiment shown in FIG. 5A, when the PSCC electrode 40 is in a relatively contact-free environment, such as air, or in the flowing blood stream while inside a blood vessel or heart chamber, the PSCC electrode 40 can be effectively an insulator. When used for an ablation application, however, the PSCC bipolar electrode system 40 can be placed against a target tissue 28, such as shown in FIG. 5B. As the contact pressure increases, the PSCC electrode 40 becomes conductive, having a conductive zone 56 and permits the degree of contact to activate and/or control operation of PSCC electrode 40, transmitting ablation energy 26 into the adjacent target tissue 28. Because of the unique properties of a PSCC electrode 40, only that portion of the PSCC electrode 40 that is in contact with the target tissue 28 becomes conductive. Those portions not in direct contact with the target tissue 28, such as the region facing the surrounding tissue 30, remain non-conductive, thereby mitigating current leakage that may cause undesired coagulum and thrombus formation in untargeted regions.

The present teachings permit the construction of a flexible, pressure-sensitive ablation electrode that can be used in a wide variety of different tissue environments, including for example, tissues having varying degrees of elasticity and contour. The present teachings further permit the construction of a flexible electrode that responds to pressure that is applied to the electrode, for example, pressure that may be applied to the electrode by the myocardium. Such electrodes may be used to respond to pressure that is applied directly to the PSCC component (for example, when the PSCC component is located at the most distal portion of a catheter), or to pressure that is applied indirectly to the PSCC (for example, when an electrode tip is disposed between the PSCC component and the tissue). When used in conjunction with an electrode tip, it is desired that the electrode tip be formed of an electrically conductive material that is relatively stiffer than the PSCC. This will permit the electrode tip to transfer pressure from the electrode tip to the PSCC component. Optionally, one or more additional pressure transfer elements may be used, for example, between the electrode tip at a distal end and the PSCC component located at a more proximal end. In the case where a PSCC component is positioned within a catheter, the PSCC component can be used to respond to pressure that is applied axially to catheter. Of course, the PSCC component could be oriented in order to respond to pressure that is applied transversely to the catheter.

While the embodiments disclosed in the attached figures disclose an electrode that is generally cylindrical in shape, the present invention also contemplates that the electrode may be formed into various shapes to better fit the contour of the target tissue. In one embodiment, for example, the electrode can be made long enough to strap around and form a noose around the pulmonary veins in epicardial applications. For example, electrical conductor 16 that is coupled to the energy source may be formed into a desired shape, and then the PSCC layer can be formed over the conductive element in the preferred shape. For example, the electrode may be shaped like a spatula for certain applications, including for example, minimally invasive sub-xyphoid epicardial applications, where the spatula shape will permit directional placement and navigation in the pericardial sac. Because PSCC can be made as a flexible material, it can be used for electrodes having a great variety of shapes, including a spatula.

Generally, flexibility is a very desirable characteristic in a catheter. Some applications, however, may require a less flexible and/or rigid catheters. Thus, as an alternative to the flexible embodiments discussed above, it is contemplated that the same structural design may be used to produce a less flexible (or even rigid or partially rigid) ablation device. For example, the PSCC electrode may use a rigid core, instead of a flexible core. It may be solid conductive core of varying degrees of rigidity, or a non-conductive core coated with a conductive layer such that the combination achieves a desired degree of rigidity. A PSCC substrate layer may then be applied to the core such that when the electrode is pressed against tissue, the PSCC becomes a conductor and electrically couples the conductive core (or layer, as the case may be) to the tissue via the PSCC. In this alternative embodiment, the PSCC may be coated with one or more outer electrically-conductive layers (which may be rigid or flexible). In this further modification, the PSCC layer can be sandwiched between at least two conductive coatings, and thus under pressure, RF energy may be delivered to the tissue via the compressible PSCC layer.

The electrically conductive element may be mounted on an electrically insulative but thermally conductive shaft. The thermally conductive shaft can improve the cooling of the electrode and the electrode-tissue interface temperature during ablation by thermally conducting heat from the interface to the ambient flowing blood in endocardial applications. In addition, the thermally conductive shaft can be equipped with thermal sensors that can be used for temperature controlled RF ablation. The thermally conductive shaft may be made of an electrically insulative, thermally conductive material, including, for example, COOLPOLY® thermally conductive, electrically insulative plastic. In an embodiment, the thermally conductive shaft is made of a biocompatible, thermally conductive, electrically insulative material.

The heat sink can comprise a material with high thermal conductivity. The use of a heat sink can be particularly useful for small electrodes typically around 10 mm or less, or for sectioned electrodes that may give rise to hot spots. The heat sink may be made of an electrically insulative, thermally conductive material, including, for example, thermally conductive polyurethane (e.g., polyurethane with thermally conductive ceramic powder embedded therein), diamond, aluminum nitride, boron nitride, silicone, thermal epoxy and thermally conductive, electrically insulative plastics. In an embodiment, the thermally conductive shaft is made of a biocompatible, thermally conductive, electrically insulative material.

The electrically insulative member 20 may provide one or more passageways for carrying filler materials 12 that are flowable (e.g. saline solution) to the distal end of the electrode and/or the electrode-tissue interface 100. The passageways include an inlet to the electrode, and an outlet at the distal end of the electrode. Moreover, one or more thermal sensors may be placed in the passageway, for example, to measure the temperature of the coolant at the inlet and at the outlet. The temperature difference between the inlet and outlet during ablation could be used to monitor the efficacy of the electrode-tissue interface cooling and also to perform temperature-controlled ablation. One or more of the passageways may be alternatively defined as a cooling tube, which may comprise the same material as, or a material different from, the electrically insulative member.

The electrically insulative tube inside the catheter shaft may be thermally insulative or may contain a thermally insulative layer. Such thermal insulation helps minimize the degree to which the flowable filler material is heated to body temperature as the result of thermal conduction through the catheter shaft wall as the fluid travels from the outside fluid source through the catheter shaft and to the electrode. The thermally conductive tube inside the electrode, on the other hand, can cool the electrode and the electrode-tissue interface during ablation by thermally conducting the heat from the interface to the flowing fluid inside the tube catheter.

In an optional embodiment, the electrodes may be combined with a processor that monitors the current that is being delivered by the power source. Thus, a computer processor (not shown) monitors the maximum current being delivered and use this information to help control the ablation process. Because a PSCC's resistance drops monotonically as pressure increases, the amount of current being delivered can be used to assess a degree of contact between the contact surface and target tissue. Using this information, the computer processor (not shown) may decrease or increase the power level of the power source. By way of example only, the computer processor (not shown) may be used to limit the total amount of energy that is delivered to a target tissue. Depending on the nature of the tissue, the power level and the total energy delivered to the electrode and the tissue may be increased or decreased to improve the safety and efficacy of lesion creation.

The PSCC used in the present invention may be chosen to have a specific pressure sensitivity. For example, highly sensitive PSCCs, which register a sharp change in resistance with a finite amount of applied pressure, may be preferred for soft contact applications such as the atrial wall. Less sensitive PSCCs, which require more pressure to register the same amount of change in resistance, may be preferred for hard contact applications such as ablation in ventricular walls.

The RF source to be used with the present invention is preferably within the radio frequency range of 100-1000 kHz, and more preferably with 250 kHz-550 kHz. The electrical energy source (RF and/or direct current source) is preferably capable of delivering up to 150 Watts of electrical power.

It is contemplated that each of the embodiments discussed above may optionally be used in connection with one or more electrically-conductive, outer coverings. Preferably, the outer covering is electrically conductive, such as a flexible wire mesh, a conductive fabric, a conductive polymer layer (which can be porous or nonporous), or a metal coating. The outer covering may be used to not only increase the mechanical integrity, but to enhance the PSCC device's ability to assess the tissue contact (for example, in the when measuring electrical characteristics using a reference electrode connected to the target tissue). In some embodiments, the outer covering may be made using a biocompatible material in order to help make the overall assembly biocompatible. Preferably the outer covering is flexible, though certain applications may prefer a medium to high degree of rigidity.

One of ordinary skill will appreciate that while the PSCC materials may be designed to respond to a variety of stresses, the principles and embodiments herein may be adapted to respond to specific stress forces, for example, axial forces, orthogonal forces, twisting, compressing, stretching, etc., without deviating from the scope of the present invention.

Although multiple embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A bipolar electrode system for ablation therapy, comprising:
    a pressure-sensitive conducting composite layer;
    a pair of electrodes in electrical communication with the pressure-sensitive conducting composite layer;
    a conductor in electrical communication with the pressure-sensitive conducting composite layer; and
    at least one pressure transfer member disposed between the pressure-sensitive conducting composite layer and at least one of the electrodes, such that pressure applied to the at least one of the electrodes is transferred through the at least one pressure transfer member to the pressure-sensitive conducting composite layer.

2. The bipolar electrode system of claim 1, further comprising:
    a catheter base coupled to one of the electrodes.

3. The bipolar electrode system of claim 1, further comprising:
    an energy source coupled to the pair of electrodes, such that ablation energy is delivered via the pressure-sensitive conducting composite layer when sufficient pressure is applied to transform the pressure-sensitive conducting composite layer to an electrical conductor.

4. The bipolar electrode system of claim 1, further comprising:
    an electrically insulative flexible layer adjacent the pressure-sensitive conducting composite layer.

5. The bipolar electrode system of claim 4, further comprising:
    one sensor located in the electrically insulative flexible layer for monitoring temperature.

6. The bipolar electrode system of claim 4, further comprising:

a heat sink thermally coupled to one of the pressure-sensitive conducting composite layer and the electrically insulative flexible layer.

7. The bipolar electrode system of claim 4, wherein the electrically insulative flexible layer includes a passageway for a filler material to cool at least one of the electrodes during ablation, said passageway comprising a loop such that a cooling fluid travels from a proximal end of at least one of the electrodes through a distal end of at least one of the electrodes and returns to the proximal end of at least one of the electrodes via the passageway.

8. The bipolar electrode system of claim 4, wherein the electrically insulative flexible layer includes a passageway for a filler material.

9. The bipolar electrode system of claim 8, wherein the passageway in the insulative flexible layer includes a wall configured to allow the filler material to circulate in the insulative flexible layer.

10. The bipolar electrode system of claim 8, wherein the electrically insulative flexible layer is permeable.

11. The bipolar electrode system of claim 8, wherein the passageway includes an outlet at a distal end of one of the electrodes, the outlet configured to permit the filler material to flow from the passageway.

12. The bipolar electrode system of claim 11, further comprising:
a first sensor configured to measure the temperature of the filler material near the outlet.

13. The bipolar electrode system of claim 12, further comprising:
a second sensor configured to measure the temperature of the filler material at a location other than the outlet.

14. The bipolar electrode of claim 12, further comprising a second sensor configured to measure the temperature of the filler material where it is configured to enter the passageway.

15. A bipolar electrode system for ablation therapy, comprising:
a pressure-sensitive conducting composite layer;
a pair of electrodes in electrical conductive contact or communication with the pressure-sensitive conducting composite layer;
a conductor in electrical conductive contact or communication with the pressure-sensitive conducting composite layer, said conductor being configured to conduct electrical energy sufficient to cause ablation;
at least one pressure transfer member disposed between the pressure-sensitive conducting composite layer and at least one of the electrodes, such that pressure applied to the at least one of the electrodes is transferred through the at least one pressure transfer member to the pressure-sensitive conducting composite layer; and
an electrically insulative flexible tube adjacent the pressure-sensitive conducting composite layer,
wherein the electrically insulative flexible tube comprises a passageway for a filler material.

16. A method of treating tissue, the method comprising:
providing an bipolar electrode system having:
a pressure-sensitive conducting composite layer;
a pair of electrodes in electrical communication with the pressure-sensitive conducting composite layer;
a conductor in electrical communication with the pressure-sensitive conducting composite layer; and
at least one pressure transfer member disposed between the pressure-sensitive conducting composite layer and at least one of the electrodes, such that pressure applied to the at least one of the electrodes is transferred through the at least one pressure transfer member to the pressure-sensitive conducting composite layer;
coupling an RF energy supply to the pair of electrodes;
operatively contacting the bipolar electrode system with a target tissue of a subject;
exerting pressure upon the target tissue through the pair of electrodes such that the pressure-sensitive conductive composite becomes conductive and delivers energy to the target tissue.

17. The method of claim 16, further comprising a heat sink thermally coupled to the bipolar electrode system.

18. A bipolar electrode system for ablation therapy, the bipolar electrode system comprising:
a catheter having a proximal end and a distal end;
a pair of electrodes for conducting energy;
a layer of quantum tunneling composite that is in electrical communication with the pair of electrodes, said layer being located at least in part at the distal end of the catheter;
a conductor that is in electrical communication with the layer of quantum tunneling composite; and
at least one pressure transfer member disposed between the layer of quantum tunneling composite and at least one of the electrodes, such that pressure applied to the at least one of the electrodes is transferred through the at least one pressure transfer member to the layer of quantum tunneling composite.

19. The bipolar electrode system of claim 18, further comprising:
an electrically insulative flexible layer adjacent the quantum tunneling composite layer.

20. The bipolar electrode system of claim 19, further comprising:
at least one sensor to measure a temperature of the electrically insulative flexible layer.

21. The bipolar electrode system of claim 19, further comprising:
a heat sink thermally coupled to at least the quantum tunneling composite layer or the electrically insulative flexible layer.

22. A bipolar electrode system for conducting ablative energy, said system comprising:
a pair of electrodes for conducting ablative energy;
a quantum tunneling composite member;
an energy source coupled to the quantum tunneling composite member;
a conductor that is in electrical contact or communication with the quantum tunneling composite member, said conductor being configured to conduct electrical energy sufficient to cause ablation; and
at least one pressure transfer member disposed between the quantum tunneling composite member and at least one of the electrodes, such that pressure that is applied to the at least one of the electrodes is transferred through the at least one pressure transfer member to the quantum tunneling composite member and causes the quantum tunneling composite member to become electrically conductive such that it conducts electrical energy to the pair of electrodes.

23. A bipolar electrode system for conducting ablative energy, said system comprising:
a pair of electrodes for conducting ablative energy;
a quantum tunneling composite member;
an energy source coupled to the quantum tunneling composite member;

a conductor that is in electrical contact or communication with the quantum tunneling composite member, said conductor being configured to conduct electrical energy sufficient to cause ablation; and at least one pressure transfer member disposed between the quantum tunneling composite member and the pair of electrodes, such that pressure applied to the pair of electrodes is transferred through the at least one pressure transfer member to the quantum tunneling composite member and causes the quantum tunneling composite member to become electrically conductive such that it conducts electrical energy to the pair of electrodes.

24. The bipolar electrode system of claim 23, further comprising a processor adapted to sense a degree of contact between at least one of the electrodes and a surface of a tissue to be ablated.

25. The bipolar electrode system of claim 23, further comprising:

a processor that monitors for a change in impedance of the quantum tunneling composite member, said processor being coupled to the energy source to control the energy being generated based on the change in impedance of the quantum tunneling composite member.

26. A method of delivering a compound to a target tissue, comprising:

providing a bipolar electrode system having:
a pressure-sensitive conducting composite layer;
a pair of electrodes in electrical contact or communication with the pressure-sensitive conducting composite layer;
a conductor in electrical communication with the pressure-sensitive conducting composite layer; and
at least one pressure transfer member disposed between the pressure-sensitive conducting composite layer and at least one of the electrodes, such that pressure applied to the at least one of the electrodes is transferred through the at least one pressure transfer member to the pressure-sensitive conducting composite layer;

providing a DC energy supply;
circulating a flowable filler material that includes the compound to be delivered to the target tissue;
operatively contacting the bipolar electrode system with a target tissue of a subject;
engaging the DC energy supply;
exerting an effective amount of pressure upon the target tissue through the pair of electrodes such that the pressure-sensitive conducting composite layer becomes conductive and delivers DC energy to the target tissue.

27. The method of claim 26, further comprising:
coupling an RF energy supply to the pair of electrodes;
disengaging the DC energy supply; and
engaging the RF energy supply.

28. The method of claim 26, wherein the compound is electrophoretic.

29. The method of claim 26, wherein the compound is photosensitive.

30. The method of claim 26, wherein the DC energy supply is electrically coupled to the pair of electrodes.

* * * * *